(12) United States Patent
Michelson

(10) Patent No.: US 7,771,475 B2
(45) Date of Patent: *Aug. 10, 2010

(54) SPINAL IMPLANT HAVING DEPLOYABLE BONE ENGAGING PROJECTIONS

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/527,377

(22) Filed: Sep. 25, 2006

(65) Prior Publication Data

US 2007/0055376 A1 Mar. 8, 2007

Related U.S. Application Data

(62) Division of application No. 10/746,183, filed on Dec. 24, 2003, now Pat. No. 7,112,206, which is a division of application No. 10/062,805, filed on Feb. 2, 2002, now Pat. No. 6,923,830.

(51) Int. Cl.
*A61F 2/44* (2006.01)

(52) U.S. Cl. .................................... 623/17.11

(58) Field of Classification Search ............... 606/61, 606/99, 104, 86 A; 623/17.11, 17.14, 17.15, 623/17.16
See application file for complete search history.

(56) References Cited

U.S. PATENT DOCUMENTS

| | | | |
|---|---|---|---|
| 2,248,054 A | 7/1941 | Becker | |
| 2,406,952 A | 9/1946 | Joesepho | |
| 4,743,256 A | 5/1988 | Brantigan | |
| 4,877,020 A | 10/1989 | Vich | |
| 5,484,437 A | 1/1996 | Michelson | |
| 5,609,635 A | 3/1997 | Michelson | |
| 5,649,931 A | 7/1997 | Bryant et al. | |
| 5,669,909 A | 9/1997 | Zdeblick et al. | |
| 5,683,394 A | 11/1997 | Rinner | |
| 5,702,391 A | 12/1997 | Lin | |
| 5,707,373 A | 1/1998 | Sevrain et al. | |
| 5,776,199 A | 7/1998 | Michelson | |

(Continued)

FOREIGN PATENT DOCUMENTS

EP 0 951 879 10/1999

(Continued)

OTHER PUBLICATIONS

International Search Report issued Sep. 11, 2003 of International Patent Application No. PCT/US03/00042, filed Jan. 23, 2003.

(Continued)

*Primary Examiner*—Eduardo C Robert
*Assistant Examiner*—David Comstock
(74) *Attorney, Agent, or Firm*—Martin & Ferraro, LLP

(57) ABSTRACT

Instrumentation is disclosed for inserting an interbody spinal fusion implant for implantation at least in part within and across the generally restored height of a disc space between two adjacent vertebral bodies of a human spine. The implant has an external housing and a substantially hollow internal rotatable member having bone engaging projections that are deployable through the housing to penetrably engage the adjacent vertebral bodies.

63 Claims, 9 Drawing Sheets

U.S. PATENT DOCUMENTS

| | | | |
|---|---|---|---|
| 5,797,909 A | 8/1998 | Michelson | |
| 5,800,547 A * | 9/1998 | Schafer et al. | 623/17.16 |
| 5,800,550 A | 9/1998 | Sertich | |
| 5,885,299 A | 3/1999 | Winslow et al. | |
| 5,888,228 A | 3/1999 | Knothe et al. | |
| 5,910,143 A | 6/1999 | Cripe et al. | |
| 6,059,829 A | 5/2000 | Schlapfer et al. | |
| 6,077,267 A | 6/2000 | Huene | |
| 6,083,225 A | 7/2000 | Winslow et al. | |
| 6,083,228 A | 7/2000 | Michelson | |
| 6,090,143 A | 7/2000 | Meriwether et al. | |
| 6,102,949 A | 8/2000 | Biedermann et al. | |
| 6,113,638 A | 9/2000 | Williams et al. | |
| 6,159,214 A | 12/2000 | Michelson | |
| 6,179,873 B1 | 1/2001 | Zientek | |
| 6,190,414 B1 | 2/2001 | Young et al. | |
| 6,210,442 B1 | 4/2001 | Wing et al. | |
| 6,224,607 B1 | 5/2001 | Michelson | |
| 6,241,770 B1 | 6/2001 | Michelson | |
| 6,371,987 B1 | 4/2002 | Weiland et al. | |
| 6,436,140 B1 | 8/2002 | Liu et al. | |
| 6,451,057 B1 | 9/2002 | Chen et al. | |
| 6,537,320 B1 | 3/2003 | Michelson | |
| 6,752,832 B2 | 6/2004 | Neumann | |
| 2002/0068977 A1 | 6/2002 | Jackson | |
| 2002/0128717 A1 | 9/2002 | Alfaro et al. | |
| 2002/0138146 A1 | 9/2002 | Jackson | |
| 2002/0161445 A1 | 10/2002 | Crozet | |
| 2003/0187436 A1 | 10/2003 | Bolger et al. | |

FOREIGN PATENT DOCUMENTS

| | | |
|---|---|---|
| WO | WO 97/46165 | 12/1997 |
| WO | WO 99/63891 | 12/1999 |
| WO | WO 01/01894 | 1/2001 |

OTHER PUBLICATIONS

U.S. Appl. No. 60/255,463, filed Dec. 2000, Michelson.

* cited by examiner

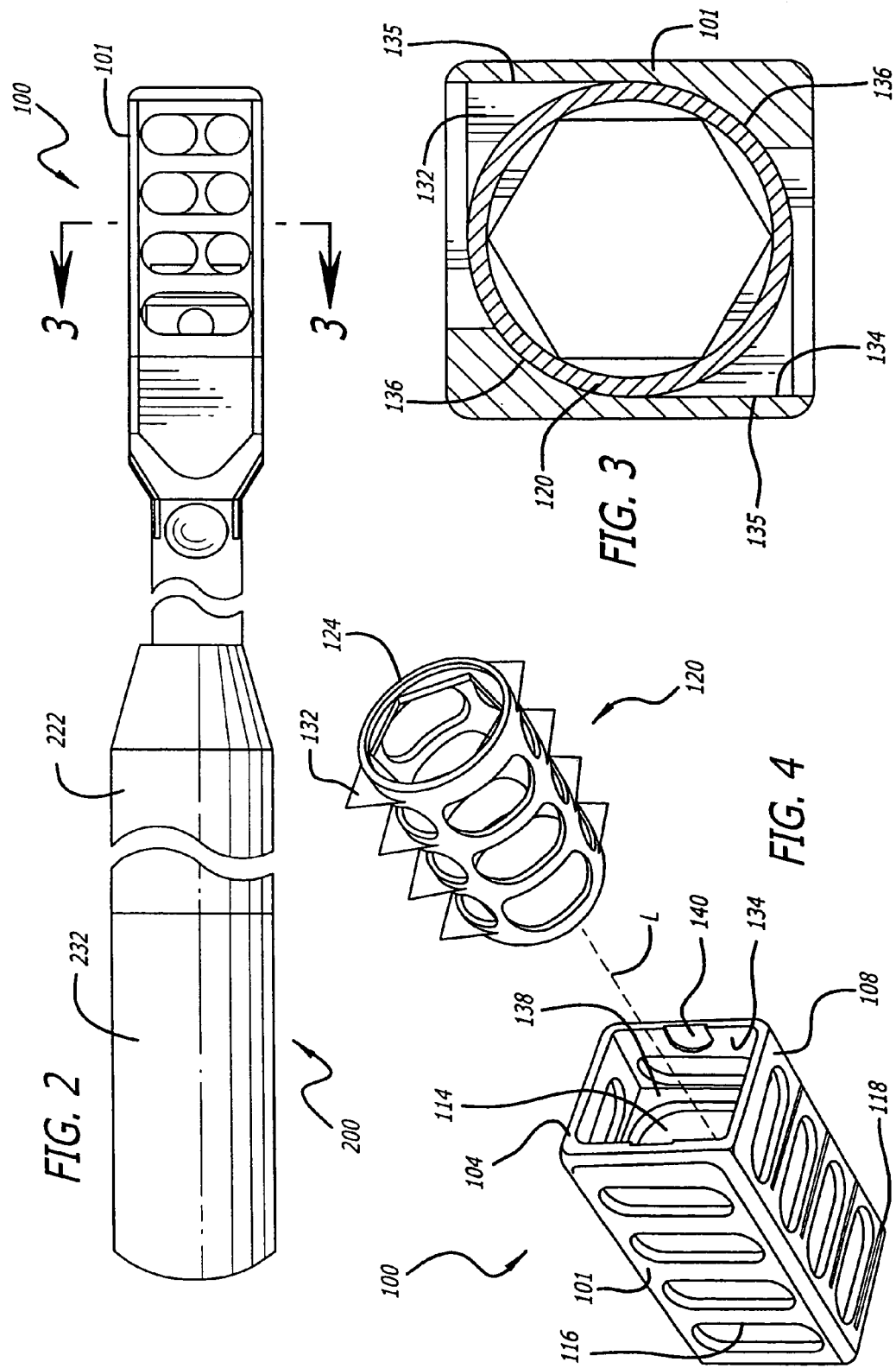

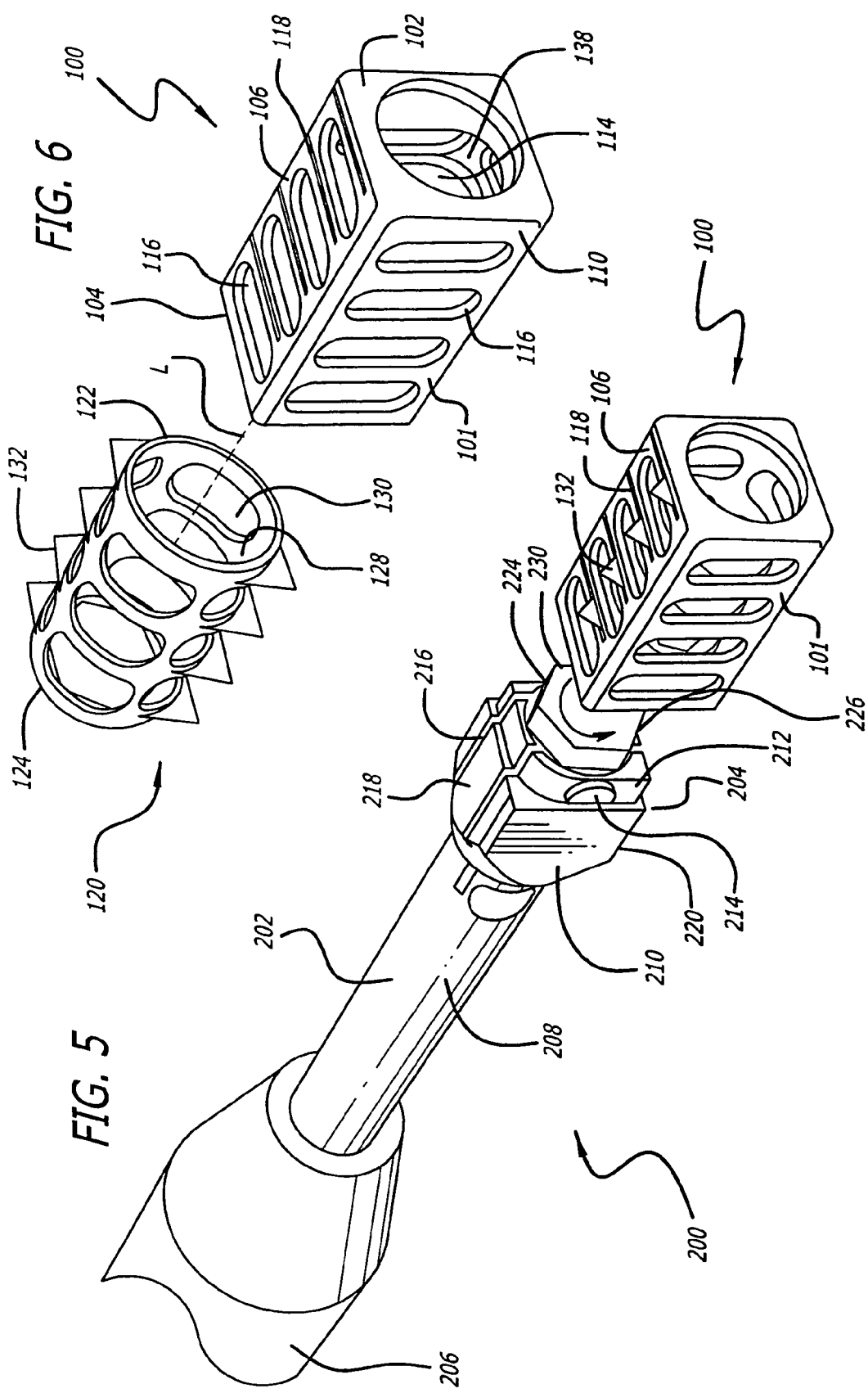

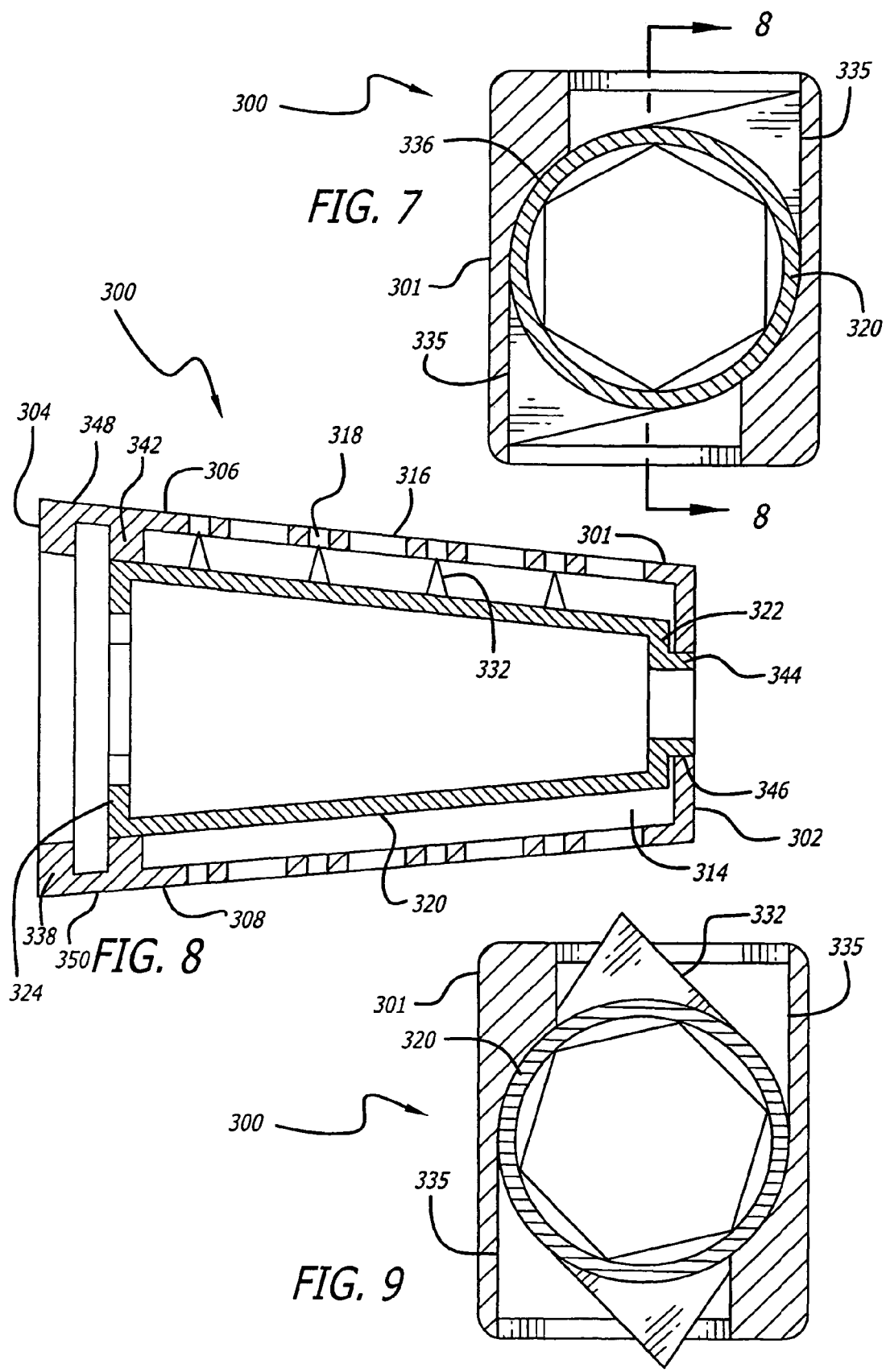

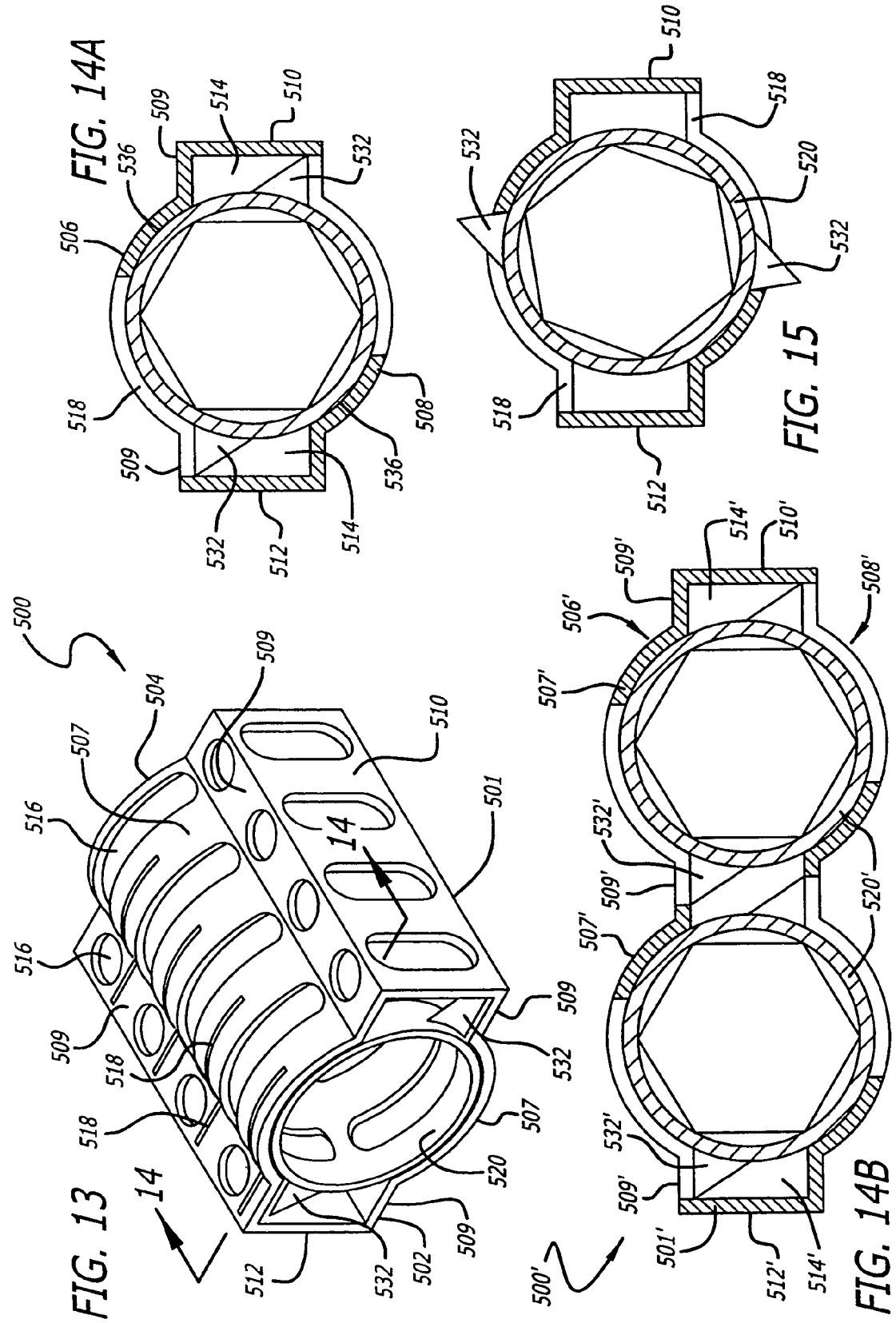

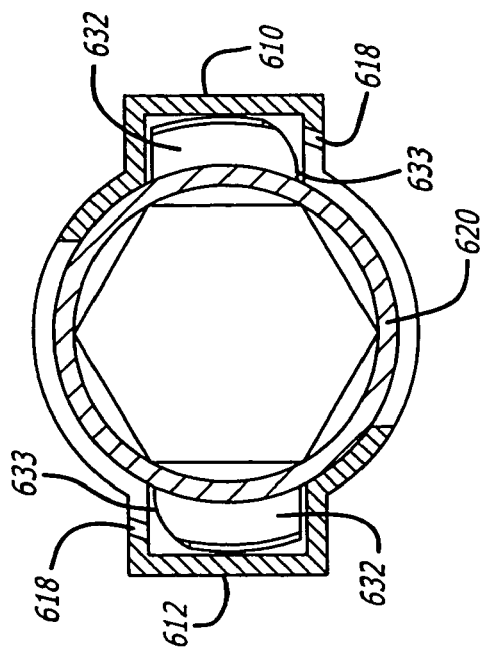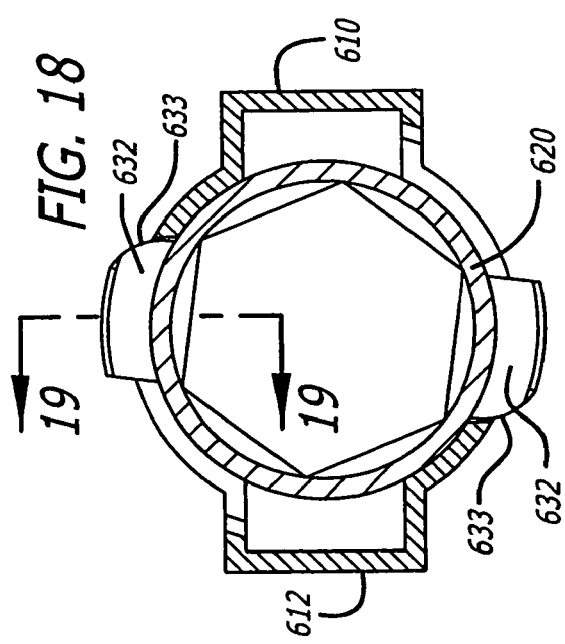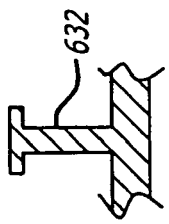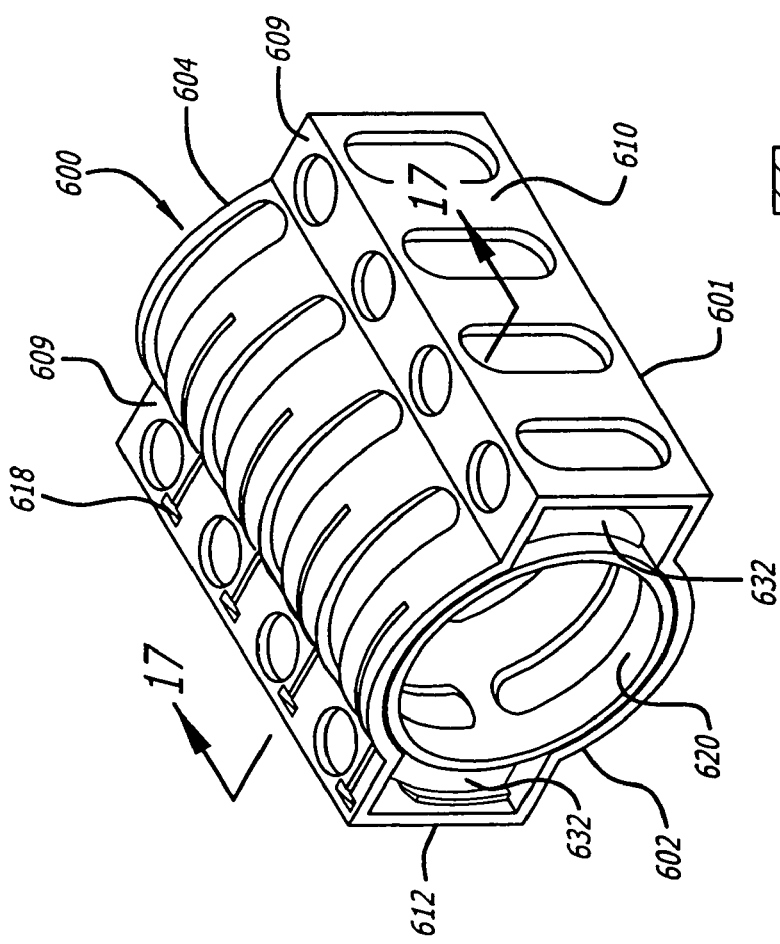

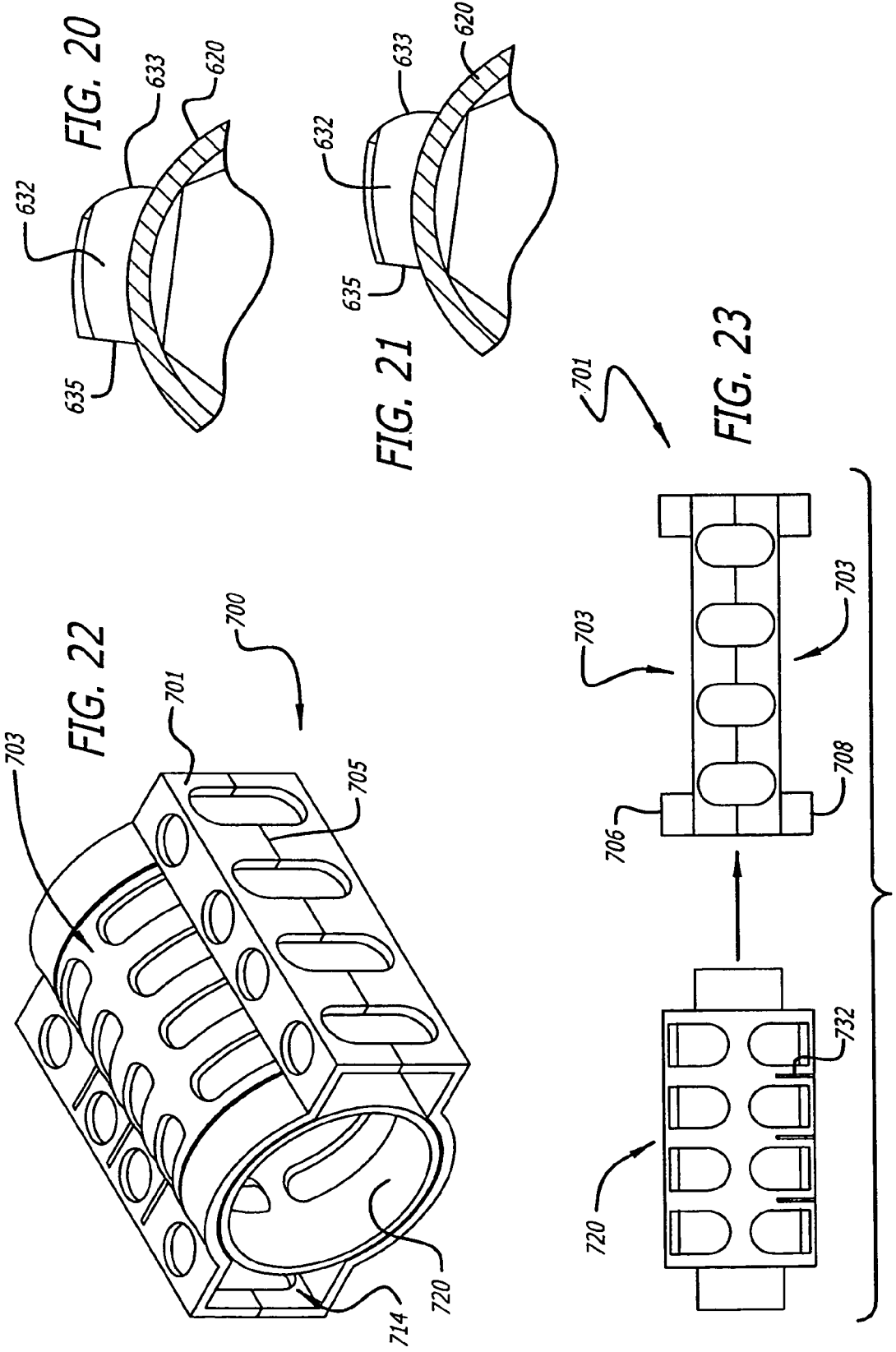

SPINAL IMPLANT HAVING DEPLOYABLE BONE ENGAGING PROJECTIONS

This application is a divisional of application Ser. No. 10/746,183, filed Dec. 24, 2003, now U.S. Pat. No. 7,112,206, which is a divisional of application Ser. No. 10/062,805, filed Feb. 2, 2002, now U.S. Pat. No. 6,923,830, all of which are incorporated herein by reference.

BACKGROUND

Push-in spinal fusion implants (allowing for the growth of bone from adjacent vertebral body to adjacent vertebral body through the implant) having upper and lower surfaces adapted for placement by linear insertion within a disc space and in contact with the adjacent vertebral bodies are known in the related art. Such a push-in spinal fusion implant was invented by Michelson and is disclosed in U.S. Pat. No. 5,776,199, filed Jun. 28, 1988, which is hereby incorporated by reference. Push-in spinal fusion implants offer the advantage of being easily positioned in the implantation space and of having the ability to have varying height to width ratios.

Lordotic or tapered, push-in spinal fusion implants are also known in the art. By way of example, Michelson has invented such implants as disclosed in U.S. Pat. No. 5,609,635, filed Jun. 7, 1995, which is hereby incorporated by reference. Lordotic or tapered, spinal fusion implants may more easily restore or enhance spinal lordosis.

Spinal fusion implants having projections that can be deployed after the implant has been inserted into the disc space are also known in the related art. An example of a spinal fusion implant having deployable projections was invented by Michelson and also is disclosed in U.S. Pat. No. 5,776,199 previously incorporated by reference herein. Other examples of implants having deployable projections include, but are not limited to, U.S. Pat. No. 6,179,873 to Zientek and International Publication No. WO 01/01894 A1 to Bolger et al. Examples of spinal fusion implants having rotatable elements for fixing the implant to the vertebrae include U.S. Pat. No. 6,210,442 to Wing et al., U.S. Pat. No. 6,090,143 to Meriwether et al., and U.S. Pat. No. 5,888,228 to Knothe et al.

None of the related art implants have a rotatable internal member with bone engaging projections that are retracted within the interior of the implant to permit the implant to be inserted into the disc space and then deployed to extend through the exterior of the implant to penetrably engage the adjacent vertebral bodies, while permitting bone growth from adjacent vertebral body to adjacent vertebral body through the interior of the implant and the interior of the internal rotatable member substantially unimpeded by the internal rotatable member and bone engaging projections.

There exists a need for a spinal fusion implant providing for all of the aforementioned features in combination.

SUMMARY OF THE INVENTION

In accordance with the present invention, as embodied and broadly described herein, there is provided a spinal fusion implant for implantation at least in part within and across the generally restored height of a disc space between two adjacent vertebral bodies of a human spine having an external housing with a substantially hollow internal rotatable member having bone engaging projections that are in a retracted position within the interior of the housing to permit the assembled implant to be inserted into the disc space. The internal rotatable member may be inserted into the housing prior to insertion of the implant into the disc space, or alternatively, the housing may be inserted into the disc space and the internal rotatable member can be subsequently inserted into the housing. The implant is preferably inserted into the disc space by linear insertion without substantial rotation of the implant. Alternatively, the implant be can be rotated at least in part generally less than 180 degrees during its implantation into the disc space and is not screwed into the disc space. After insertion, the internal rotatable member is rotated to a deployed position so that the bone engaging projections extend through the exterior of the housing to penetrably engage the adjacent vertebral bodies to resist expulsion of the implant from the disc space, to gain access to the more vascular bone of the vertebral bodies further from the bone surfaces adjacent the disc space, to stabilize the adjacent vertebral bodies relative to the implant, and to stabilize the vertebral bodies relative to each other. The spinal implant is configured to permit bone growth from adjacent vertebral body to adjacent vertebral body through the housing and through the interior of the internal rotatable member preferably substantially unimpeded by further internal mechanisms.

In one embodiment, the spinal implant of the present invention has an external housing having a hollow interior and a substantially hollow rotatable member therein. The implant and each of the hollow components, that is the housing and the internal rotatable member, are adapted to hold fusion promoting substances, such as but not limited to bone. The housing preferably has relatively thin walls, openings, and except for the openings preferably a relatively smooth exterior. The rotatable member has an open interior configured to hold bone growth promoting material and at least one aperture therethrough in communication with the open interior to permit for the growth of bone therethrough. The rotatable member preferably, but not necessarily, has a generally cylindrical or frusto-conical configuration, is preferably thin-walled, and is preferably in contact with the external housing, but is free to rotate therein sufficient for its intended purpose. The rotatable member has bone engaging projections adapted to penetrably engage the bone of the adjacent vertebral bodies by rotating the rotatable member. The rotatable member is adapted to rotate within the hollow interior of the implant between a retracted position and a deployed position. The bone engaging projections extend through at least some of the openings in the upper and lower surfaces of the implant so as to penetrate the vertebral bodies adjacent the disc space to be fused deep to the adjacent superficial endplate surfaces when deployed.

In a preferred embodiment, the bone engaging projections have a blade-like configuration oriented transverse to the longitudinal axis of the rotatable member with a leading edge and a trailing edge angled relative to each other to form an apex adapted to penetrate the bone of a vertebral body. The bone engaging projections are preferably oriented on opposite sides of the rotational member and may, but need not, be diametrically opposite one another. The bone engaging projections may be arranged such that at least the apexes of two opposite bone engaging projections are on opposite sides of a mid-line passing therethrough. Such an over-center arrangement of the bone engaging projections creates a more stable configuration of the implant when the bone engaging projections are fully deployed. Greater energy is required to de-rotate the rotatable member with opposed bone engaging projections in an over-center arrangement as the apex of each bone engaging projection has to be moved through the mid-line to move from a deployed to a retracted position.

The spinal implants of the present invention may have upper and lower surfaces that are generally parallel or angled relative to one another. The spinal implants of the present invention may have a cross-section transverse to the longitudinal axis of the implant that is generally square, rectangular, or any other configuration suitable for its intended purpose. The spinal implants of the present invention may have the width equal to the height, the width greater than the height, or the width less than the height. The spinal implants of the present invention may have more than one rotatable member with bone engaging projections. The rotatable member can have a generally cylindrical configuration, a generally frusto-conical configuration, or any other configuration suitable for the intended purpose.

The present invention is also directed to an implant inserter instrument adapted to insert the spinal implant into an implantation site and deploy the bone engaging projections. The inserter instrument is configured to cooperatively engage the trailing end of the implant to rotate the rotatable member to deploy the bone engaging projections. The present invention is also directed to the methods for inserting and deploying a spinal implant in accordance with the present invention.

BRIEF DESCRIPTION OF THE DRAWINGS

FIG. 2 is a fragmented side elevation view of the inserter instrument and implant of FIG. 1.

FIG. 3 is a cross sectional view of the implant of FIG. 1 taken along line 3-3 of FIG. 2.

FIG. 4 is an exploded perspective view of the trailing end of the implant of FIG. 1 and the rotatable member having deployable bone engaging projections.

FIG. 5 is a partial perspective view of the leading end of the implant and the inserter instrument of FIG. 1 shown with bone engaging projections in a deployed position.

FIG. 6 is an exploded perspective view of the leading end of implant of FIG. 1.

FIG. 7 is a cross sectional end view of another embodiment of an implant with the bone engaging projections in a retracted position in accordance with the present invention.

FIG. 8 is a cross sectional side view of the implant of FIG. 7 taken along line 8-8 of FIG. 7.

FIG. 9 is a cross sectional end view of the implant of FIG. 7 with the bone engaging projections in a deployed position.

FIG. 13 is a front perspective view of another embodiment of an implant in accordance with the present invention with the bone engaging projections in a retracted position.

FIG. 14A is a cross sectional view along line 14-14 of FIG. 13.

FIG. 14B is a cross sectional view similar to FIG. 14A of an alternative embodiment of an implant in accordance with the present invention.

FIG. 15 is a cross sectional view along line 14-4 of FIG. 13 with the bone engaging projections in a deployed position.

FIG. 16 is a front perspective view of another embodiment of an implant in accordance with the present invention with the bone engaging projections in a retracted position.

FIG. 17 is a cross sectional view along line 17-17 of FIG. 16.

FIG. 18 is a cross sectional view along line 17-17 of FIG. 16 with the bone engaging projections in a deployed position.

FIG. 19 is a fragmented cross sectional view along line 19-19 of FIG. 18.

FIG. 20 is an enlarged fragmentary view of a rotatable member and a bone engaging projection of another preferred embodiment of an implant in accordance with the present invention.

FIG. 21 is an enlarged fragmentary view of a rotatable member and a bone engaging projection of yet another preferred embodiment of an implant in accordance with the present invention.

FIG. 22 is a front perspective view of another preferred embodiment of an implant in accordance with the present invention with the bone engaging projections in a retracted position.

FIG. 23 is an exploded side elevation view of the implant of FIG. 22.

DETAILED DESCRIPTION OF THE DRAWINGS

Figure 1:
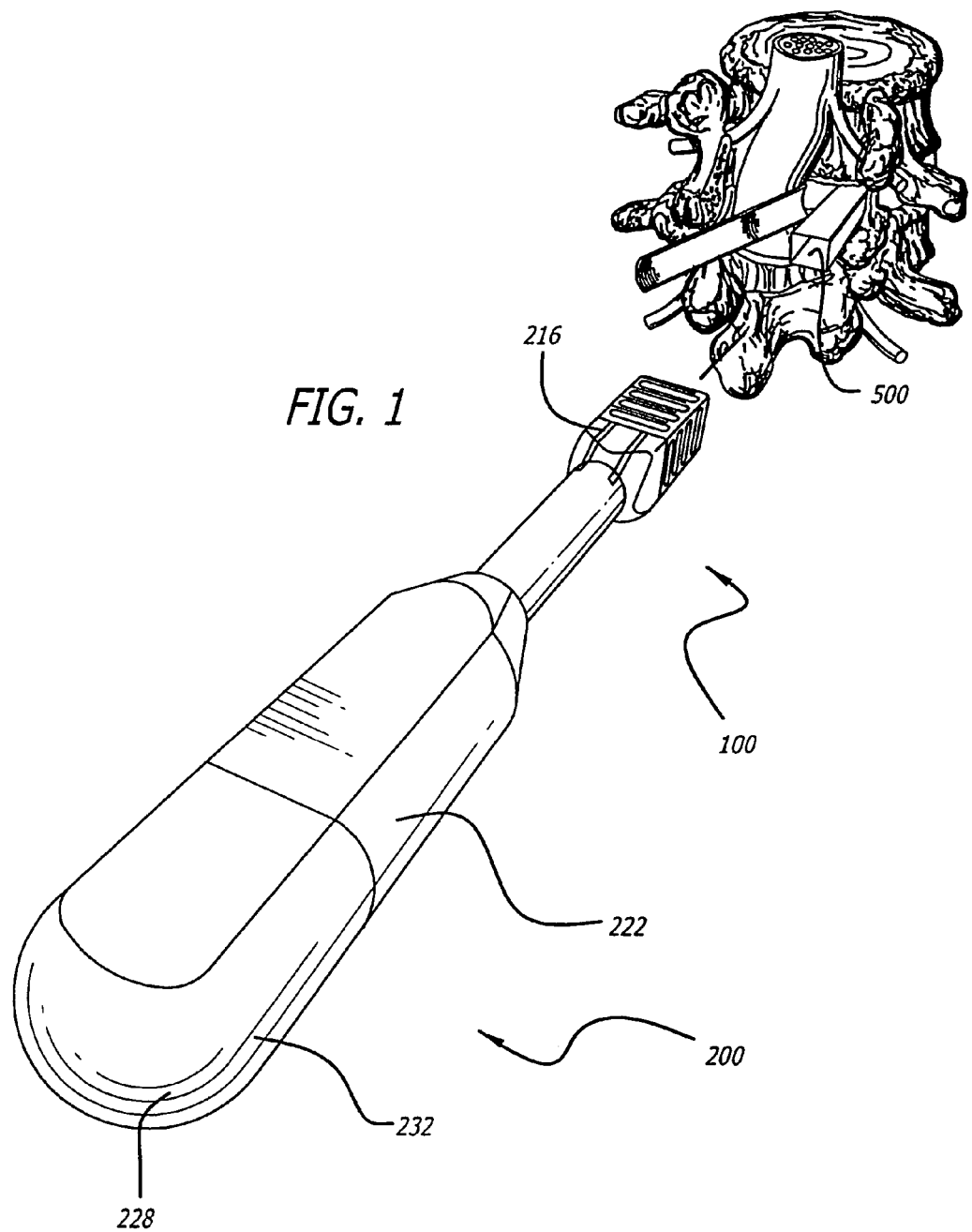
FIG. 1 is a rear perspective view of a lumbar segment of a spine with the dural sac retracted to the left showing a prepared recipient implantation site with a guard for providing guided access to the disc space and an embodiment of an inserter instrument and an embodiment of an implant in accordance with the present invention attached thereto approaching the disc space between the adjacent vertebral bodies.

Reference will now be made in detail to the present preferred embodiments (exemplary embodiments) of the invention, examples of which are illustrated in the accompanying drawings. Wherever possible, the same reference numbers will be used throughout the drawings to refer to the same or like parts.

FIGS. 1-6 show a preferred embodiment of a spinal implant 100 and a preferred embodiment of an implant inserter 200 in accordance with the present invention. Implant 100 has an external housing 101 with a leading end 102 for insertion first into the disc space between two adjacent vertebral bodies of the human spine, a trailing end 104 opposite leading end 102, an upper surface 106, a lower surface 108, and sides 110, 112 between upper and lower surfaces 106, 108. Leading end 102 may be tapered to facilitate insertion of implant 100 into the disc space. Housing 101 of implant 100 preferably has at least a portion along its longitudinal axis L that has a generally square cross section transverse to the longitudinal axis L. It is appreciated that housing 101 can have a generally rectangular cross section or other cross-sectional configuration suitable for its intended purpose. Housing 101 preferably has a hollow interior 114 configured to hold bone growth promoting material. In this embodiment, upper and lower surfaces 106, 108 are preferably at least in part non-arcuate. Upper and lower surfaces 106, 108, of housing 101 preferably each have at least one opening 116 in communication with hollow interior 114 and adapted to permit the growth of bone from adjacent vertebral body to adjacent vertebral body through housing 101. Upper and lower surfaces 106, 108 further preferably have a plurality of openings 118 configured to permit the passage therethrough of bone engaging projections 132 described below from hollow interior 114 to the exterior of housing 101. Sides 110, 112 of implant 100 can also have openings 116.

Implant 100 has an internal rotatable member 120 configured to be preferably at least in part within hollow interior 114 of housing 101 and as shown in this embodiment is insertable within hollow interior 114 by the user. While in this embodiment, rotatable member 120 is shown entirely within hollow interior 114 of housing 101, it is appreciated that the rotatable member need not be entirely within hollow interior 114. For example, the rotatable member may have an external flange that is at least in part outside of hollow interior 114. Rotatable member 120 is preferably substantially hollow and has a leading end 122, a trailing end 124, an exterior surface 126, and an open interior 128. Trailing end 124 preferably is configured to cooperatively engage an instrument for rotating rotatable member 120 such as, for example, inserter 200 (described below). For example, the inner perimeter of trailing end 124 can be hex-shaped or have any other configuration suitable for cooperatively engaging an instrument for rotating rotatable member 120. Exterior surface 126 of rotatable member 120 preferably has at least one opening 130 that permits bone to grow therethrough. Preferably, at least one of openings 130 in rotatable member 120 is configured to generally align with at least one of openings 116 in housing 101 to allow bone to grow from adjacent vertebral body to adjacent vertebral body though housing 101 and through rotatable member 120.

The upper and lower surfaces of rotatable member 120 have at least one bone engaging projection 132 adapted to penetrably engage the bone of the adjacent vertebral bodies. Bone engaging projections 132 are preferably configured such that when rotatable member 120 is in a retracted position, implant 100 may be linearly inserted into the disc space. After implant 100 is inserted into the disc space, rotatable member 120 is moved to a deployed position so that bone engaging projections 132 penetrably engage the endplates of an adjacent vertebral body and prevent expulsion of implant 100 from the disc space.

In a preferred embodiment, bone engaging projections 132 have a blade-like configuration oriented transverse to the longitudinal axis of rotatable member 120 with a leading edge and a trailing edge angled relative to each other to form an apex adapted to penetrate the bone of a vertebral body. The blade-like bone engaging projections 132 are preferably of appropriate thickness, shape and sharpness to penetrate the vertebral bodies adjacent the disc space to be fused deep to the adjacent superficial endplate surfaces when the implant is in the deployed position. Bone engaging projections 132 are preferably oriented on opposite sides of rotational member 120 and may, but need not, be diametrically opposite one another. Bone engaging projections 132 may be arranged such that at least the apexes of two opposite bone engaging projections 132 are on opposite sides of a mid-line passing therethrough. Such an over-center arrangement of bone engaging projections 132 creates a more stable configuration of the implant when the bone engaging projections are fully deployed. Greater energy is required to de-rotate a rotatable member with opposed bone engaging projections when in an over-center arrangement as the apex of each bone engaging projection has to be moved through the mid-line to move from a deployed to a retracted position.

As will be appreciated by those skilled in the art, bone engaging projections other than blades may be employed that are suitable for the intended purpose. The number and orientation of the bone engaging projections along rotatable member 120 may be varied without departing from the broad scope of the present invention. For example, at least two of the bone engaging projections may be arranged at an angle to the outer surface of rotatable member 120, the angle may be 90 degrees or an angle other than 90 degrees to enhance the resistance of implant 100 to expulsion from the disc space. As another example, bone engaging projections 132 may also be oriented parallel to one another along at least a portion of the longitudinal axis of implant 100.

As shown in FIG. 3, interior surface 134 of hollow interior 114 of housing 101 preferably forms a pair of opposed abutment surfaces 136. Abutment surfaces 136 are configured to support and permit rotatable member 120 to rotate within hollow interior 114 from a retracted to a deployed position to deploy bone engaging projections 132. The rotation of rotatable member 120 is limited when bone engaging projections 132 contact abutment surfaces 136. The rotation of rotatable member 120 can be limited to approximately 180 degrees or less about its axis of rotation so that it takes a half turn or less of the rotatable member to deploy the bone engaging projections. By way of example only and not limitation, the rotation of rotatable member 120 can be limited to a range of approximately 25 degrees to approximately 65 degrees to move bone engaging projections from a retracted to a deployed position. Abutment surfaces 136 also may be configured to limit the rotation of rotatable member 120 to approximately 90 degrees or less about its axis of rotation so that it takes a quarter turn or less of the rotatable member to deploy the bone engaging projections. Interior surface 134 of hollow interior 114 preferably has spaces 135 within the hollow interior 114 of housing 101 configured to receive bone engaging projections 132 in the retracted position such that the apex of each bone engaging projection is substantially in a corner of hollow interior 114. In this position, the bone engaging projections are retained substantially within the hollow interior of housing 101.

Abutment surfaces 136 also preferably form a shoulder 138 within hollow interior 114 proximate trailing end 104 of housing 101 that is configured to permit and support the insertion of rotatable member 120 into hollow interior 114 and retain rotatable member 120 therein in the deployed position. Shoulder 138 also is preferably configured to contact implant an engagement surface 212 of inserter 200 as will be described below. The interior surface of hollow interior 114 also preferably has a pair of opposed grooves 140 proximate trailing end 104 that are adapted to engage tabs 214 of inserter 200. It is appreciated that trailing end 104 may have any configuration known to those skilled in the art suitable for cooperatively engaging an appropriate insertion instrument.

As shown in FIGS. 5 and 6, rotatable member 120 is insertable into hollow interior 114 of housing 101. After rotatable member 120 is inserted into hollow interior 114 and implant 100 is inserted into the disc space, rotatable member 120 is rotated such that bone engaging projections 132 extend through openings 118 to project above upper and lower surfaces 106, 108 of housing 101. It is appreciated that upper and lower surfaces 106, 108 can have any openings suitable for the intended purpose of deploying bone engaging projections or other means for achieving the same purpose. Further, openings 118 can be in the form of slots wherein the slots are configured to be in close tolerance with bone engaging projections 132 so as to support bone engaging projections 132 when deployed.

As shown in FIG. 4, hollow interior 114 of housing 101 and open interior 128 of rotatable member 120 are configured to hold bone growth materials therein. Examples of such bone growth materials include, but are not limited to, any of, or any combination of, bone in any of its forms, materials derived from bone, bone morphogenetic proteins, mineralizing proteins, genetic materials coding for the production of bone or any substance capable of inducing the formation of bone or useful for achieving fusion for the intended purpose. The rotation of rotatable member 120, when rotated between a retracted and a deployed position, does not substantially displace bone growth material from within hollow interior 114 of housing 101 and/or open interior 128 of rotatable member 120. Accordingly, implant 100 and rotatable member 120 can be loaded with bone growth material prior to insertion of the implant into the disc space and prior to deployment of the bone engagement projections. Alternatively, housing 101 and rotatable member 120 can be loaded with bone growth material after insertion of the implant at least in part within the disc space either before or after rotation of rotatable member 120 and may be further loaded after deployment of the bone engaging projections as desired.

FIGS. 1, 2 and 5 show a preferred implant inserter 200 for use with the implant of the present invention. Inserter 200 preferably has an outer shaft 202 with a distal end 204, a proximal end 206, and a reduced diameter medial portion 208. Distal end 204 preferably has a head portion 210 with an implant engagement surface 212 located distally thereto. Head portion 210 preferably has a cross section transverse to the longitudinal axis of inserter 200 corresponding to the transverse cross sectional configuration of at least the outer perimeter of trailing end 104 of implant 100.

Implant engagement surface 212 is preferably sized and shaped to cooperatively contact shoulder 138 of hollow interior 114 of housing 101. Implant engagement surface 212 also preferably has opposed tabs 214 that are adapted to snap into grooves 140 of housing 101.

Head portion 210 also preferably has a pair of longitudinal recesses 216 extending between an upper surface 218 and a lower surface 220 of head portion 210. Recesses 216 permit head portion 210 to be resiliently compressed so that tabs 214 may be inserted into grooves 140 of housing and then locked into place when released. Outer shaft 202 also preferably has a handle 222 at its proximal end 206.

Inserter 200 also has an inner shaft 224 that is rotatable within outer shaft 202. Inner shaft 224 has a distal end 226 and a proximal end 228. Distal end 226 of inner shaft 224 has rotational engagement surface 230 that is preferably configured to cooperatively engage trailing end 124 of rotatable member 120. In a preferred embodiment, rotational engagement surface 230 is hex-shaped. Proximal end 228 of inserter 200 preferably has a handle 232 with an outer perimeter corresponding to the outer perimeter of handle 222 of outer shaft 202. Handle 232 is preferably proximal of handle 222 so that the surgeon may rotate inner shaft 224 via handle 232 while holding handle 222. In a preferred embodiment, inserter 200 preferably stabilizes housing 101 of implant 100 while rotating rotatable member 120 to deploy bone engaging projections 132. Inserter 200 is preferably a combination holder, driver, extractor, housing stabilizer, and rotator all in one.

While a preferred embodiment of an inserter 200 is shown, it is appreciated that any other inserter suitable for the intended purpose known to those skilled in the art may be used to insert the implants of the present invention.

In FIGS. 7-9, another preferred embodiment of the implant of the present invention is shown and generally referred to by the reference number 300. Implant 300 is similar to implant 100 but has a height that is greater than its width. Implant 300 preferably has a housing 301 with upper and lower surfaces 306, 308 that are angled with respect to one another so as to maintain the natural lordosis of the spine after implantation. For example, upper and lower surfaces 306, 308 may be in a diverging or converging angular relationship to each other along at least a portion of the longitudinal axis of implant 300. Similarly, sides 310, 312 can be angled relative to one another. It is appreciated that implant upper and lower surfaces 306, 308 and sides 310, 312 need not be angled.

Implant 300 has a rotatable member 320 that is preferably frustoconical in shape. Rotatable member 320 has bone engaging projections 332 adapted to penetrably engage the bone of the adjacent vertebral bodies. Bone engaging projections 332 are preferably configured such that in a retracted position, implant 300 may be linearly inserted into the disc space. After implant 300 is inserted into the disc space, bone engaging projections 332 are moved to a deployed position to penetrably engage the endplates of each adjacent vertebral body and prevent the expulsion of implant 300 from the disc space. The rotation of rotatable member 320 can be limited to approximately 180 degrees or less about its axis of rotation so that it takes a half turn or less of the rotatable member to deploy the bone engaging projections. By way of example only and not limitation, the rotation of rotatable member 320 can be limited to a range of approximately 25 degrees to approximately 65 degrees to move bone engaging projections from a retracted to a deployed position.

To support and facilitate the rotation of rotatable member 320, hollow 314 of housing 301 preferably has a second shoulder 342 proximate to a first shoulder 338. First shoulder 338 is preferably configured for engagement with the distal end of a suitably configured inserter 200. Second shoulder 342 supports a trailing end 324 of rotatable member 320. A leading end 322 of rotatable member 320 preferably has a cylindrical extension 344 for insertion into an opening 346 at leading end 302 of housing 301. Cylindrical extension 344 serves as an axle to support leading end 322 and permit rotation of rotatable member 320 within hollow 314 of implant 300. Rotatable member 320 may have openings in its surface along its longitudinal axis to permit bone to grow through rotatable member 320 and have an open interior.

Figure 10:
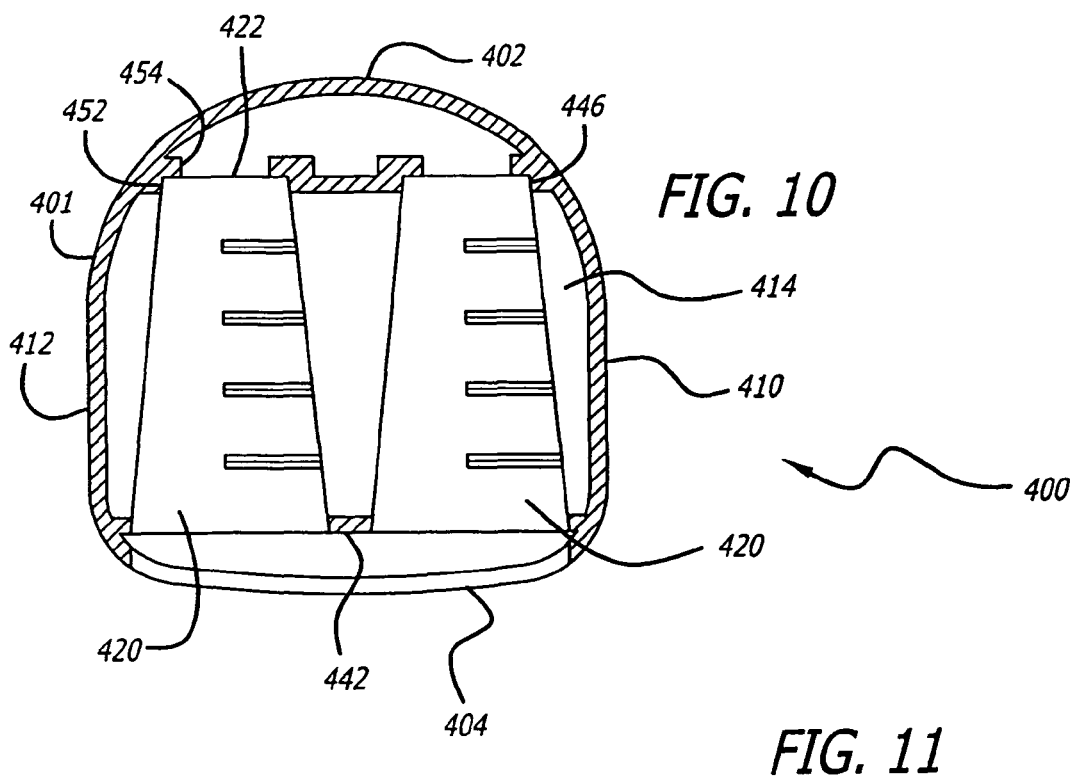
FIG. 10 is a cross sectional top view of another embodiment of an implant in accordance with the present invention.
Figure 11:
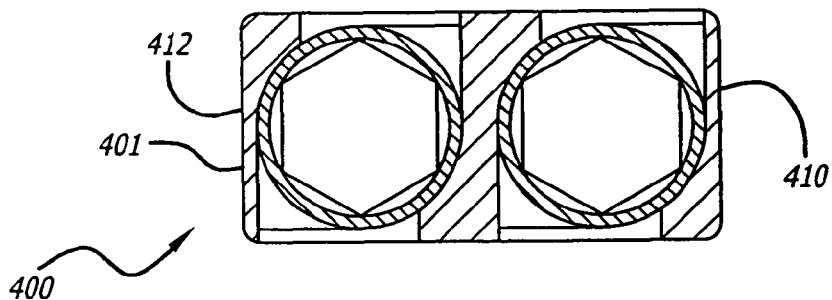
FIG. 11 is a cross sectional trailing end view of the implant of FIG. 10 with the bone engaging projections in a retracted position.
Figure 12:
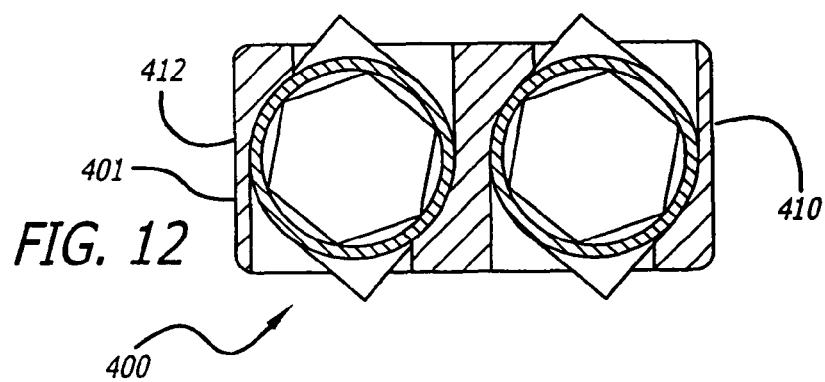
FIG. 12 is a cross sectional end view of the implant of FIG. 10 with bone engaging projections in a deployed position.

In FIGS. 10-12, another preferred embodiment of the implant of the present invention for insertion into the spine from an anterior approach is shown and generally referred to by the reference number 400. Implant 400 is similar to implant 300 except that it has a width greater than its height and has two rotatable members 420 within hollow interior 414 of housing 401. Housing 101 preferably has upper and lower surfaces 406, 408 that are angled with respect to one another and an overall width that is generally greater than one half the width of the disc space into which implant 400 is to be inserted.

Trailing end 404 of housing 401 may have an anatomical configuration to utilize the apophyseal rim bone around the perimeter of each vertebral body to help support the implant, and/or avoid the need to deeply countersink the implant so as to avoid a lateral corner of the implant from protruding beyond the perimeter of the vertebral bodies. Examples of such configurations are in U.S. Pat. No. 6,241,770 to Michelson, entitled "Implant with Anatomically Conformed Trailing End," the disclosure of which is hereby incorporated by reference. Housing 401 has internal openings 446 proximate leading end 402 configured to support rotatable members 420 and are preferably configured to have a wider diameter portion 452 and a reduced diameter portion 454. Wider diameter portion 452 is configured to receive and support leading end 422 of a rotatable member 420 while reduced diameter portion 454 acts as a stop to prevent rotatable member 420 from moving toward leading end 402 of housing 401.

Rotatable members 420 are positioned to either side of the mid-longitudinal axis of housing 401. The rotatable members may be adapted to rotate in the same or opposite directions.

In FIGS. 13-15, another preferred embodiment of the implant of the present invention is shown and generally referred to by the reference number 500. Implant 500 has an external housing 501 with a leading end 502 for insertion first into the disc space between two adjacent vertebral bodies of the human spine, a trailing end 504 opposite leading end 502, an upper surface 506, a lower surface 508, and sides 510, 512 between upper and lower surfaces 506, 508. Housing 501 of implant 500 has a hollow interior 514 configured to hold bone growth promoting material. In this embodiment, upper and lower surfaces 506, 508 each preferably have at least an arcuate portion 507 and at least a non-arcuate portion 509 near sides 510, 512. Non-arcuate portions 509 of upper and lower surfaces 506, 508 are adapted to be oriented toward the endplates adjacent the disc space and are configured to support the adjacent vertebral bodies when implant 500 in inserted into the disc space. Arcuate portions 507 of upper and lower surfaces 506, 508 are adapted to be inserted into an implantation space formed across the height of the disc space and into the adjacent vertebral bodies. Such an implantation space may be formed with a bone removal device, such as but not limited to, a drill, a trephine, a reamer, a burr, and any other bone removal device known to those skilled in the art suitable for its intended purpose.

Upper and lower surfaces 506, 508, of implant 500 preferably each have at least one opening 516 in communication with hollow interior 514 of housing 501 and adapted to permit the growth of bone from adjacent vertebral body to adjacent vertebral body through implant 500. Upper and lower surfaces 506, 508 further preferably have a plurality of openings 518 configured to permit the passage therethrough of bone engaging projections 532 described below from hollow interior 514 to the exterior of housing 501. Sides 510, 512 of implant 500 can also have openings 516.

Implant 500 has an internal rotatable member 520 configured to be inserted into hollow interior 514 of housing 501 preferably through an opening at trailing end 504 of implant housing 501. Alternatively, housing 501 of implant 500 need not be one piece, such as for example housing 501 may be split into upper and lower portions. With the upper and lower portions apart, rotatable member 520 can be placed into hollow interior 514 and then housing 501 can be reassembled by putting together upper and lower portions and implant 500 can then be inserted into the disc space. In this manner, bone engaging projections 532 may be at least in part within the thickness of the wall of housing 501 when in openings 518 and not extend beyond the exterior of implant 500 in the retracted position.

Rotatable member 520 is preferably substantially hollow and has a leading end 522, a trailing end 524, an exterior surface 526, and an open interior 528. Trailing end 524 preferably is configured to cooperatively engage an instrument for rotating rotatable member 520 such as, for example, an inserter similar to inserter 200 described above. Exterior surface 526 of rotatable member 520 preferably has at least one opening 530 that permits bone to grow therethrough. Preferably, at least one of openings 530 in rotatable member 520 is configured to generally align with at least one of openings 516 in housing 501 to allow bone to grow from adjacent vertebral body to adjacent vertebral body through housing 501 and through rotatable member 520.

The upper and lower surfaces of rotatable member 520 have at least one bone engaging projection 532 adapted to penetrably engage the bone of the adjacent vertebral bodies similar to bone engaging projections 132 described above. Bone engaging projections 532 are preferably configured such that when rotatable member 520 is in a retracted position, implant 500 may be linearly inserted into the disc space. After implant 500 is inserted into the disc space, rotatable member 520 is moved to a deployed position so that bone engaging projections 532 penetrably engage into the adjacent vertebral bodies. The rotation of rotatable member 520 can be limited to approximately 180 degrees or less about its axis of rotation so that it takes a half turn or less of the rotatable member to deploy the bone engaging projections. By way of example only and not limitation, the rotation of rotatable member 520 can be limited to a range of approximately 45 degrees to approximately 100 degrees to move bone engaging projections from a retracted to a deployed position.

Bone engaging projections 532 are preferably oriented on opposite sides of rotational member 520 and may, but need not, be diametrically opposite one another. Bone engaging projections 532 may be arranged such that at least the apexes of two opposite bone engaging projections 532 are on opposite sides of a mid-line passing therethrough. Such an over-center arrangement of bone engaging projections 532 creates a more stable configuration of the implant when the bone engaging projections are fully deployed. Greater energy is required to de-rotate a rotatable member with opposed bone engaging projections when in an over-center arrangement as the apex of each bone engaging projection has to be moved through the mid-line to move from a deployed to a retracted position.

As shown in FIG. 14A, interior surface 534 of hollow interior 514 of housing 501 preferably forms a pair of opposed abutment surfaces 536. Abutment surfaces 536 are configured to support and permit rotatable member 520 to rotate within hollow interior 514 from a retracted to a deployed position to deploy bone engaging projections 532. The rotation of rotatable member 520 is limited when bone engaging projections 532 contact abutment surfaces 536. The rotation of rotatable member 520 can be limited to approximately 180 degrees or less about its axis of rotation so that it takes a half turn or less of the rotatable member to deploy the bone engaging projections. Abutment surfaces 536 also may be configured to limit the rotation of rotatable member 520 to approximately 90 degrees or less about its axis of rotation so that it takes a quarter turn or less of the rotatable member to deploy the bone engaging projections. Interior surface 534 of hollow interior 514 preferably has spaces configured to receive bone engaging projections 532 in the retracted position such that the apex of each bone engaging projection is substantially in a corner of hollow interior 514. In this position, the bone engaging projections are retained substantially within the hollow interior of housing 501.

In FIG. 14B, another preferred embodiment of the implant in accordance with the present invention is shown and generally referred to by the reference number 500'. Implant 500' is similar to implant 500, except that upper and lower surfaces 506', 508' each preferably having at least two arcuate portions 507' and at least some non-arcuate portion 509' either between or lateral to arcuate portions 507' and/or near sides 510', 512'. Non-arcuate portions 509' of upper and lower surfaces 506', 508' are adapted to be oriented toward the vertebral bodies and, if still present, the endplates adjacent the disc space and are configured to support the adjacent vertebral bodies when implant 500' is inserted into the disc space. Arcuate portions 507' of upper and lower surfaces 506', 508' are preferably located on opposite sides of the mid-longitudinal axis of implant 500'. Such a configuration helps to further reduce or eliminate any potential rocking motion that might otherwise occur with an implant having a centrally placed single arcuate portion. Arcuate portions 507' may be generally parallel to each other or at an angle to each other. Having two or more arcuate portions 507' provides for more surface area of implant 500' to contact the bone of the adjacent vertebral bodies and may also provide for access to the vascular bone of the adjacent vertebral bodies. Implant 500' having at least two arcuate portions 507' has a height that is less than an implant with a single arcuate portion having the same combined width of two arcuate portions 507'. Furthermore, implant 500' having at least two arcuate portions 507' provides the added advantage of utilizing the stronger more dense bone of the adjacent vertebral bodies located closer to the disc space.

Implant 500' preferably has at least two internal rotatable members 520' configured to be inserted into hollow interior 514' of housing 501' preferably through an opening at one of the trailing and leading ends of implant housing 501' or the implant may be opened, such as by way of example only by having the upper and lower portions of the housing configured to be separable, to permit the placement of rotatable members 520' into hollow interior 514'. Then, housing 501' can be reassembled by putting together upper and lower portions and implant 500' can then be inserted into the disc space.

In FIGS. 16-19, another preferred embodiment of the implant of the present invention is shown and generally referred to by the reference number 600. Implant 600 is similar to implant 500 except for the configuration of bone engaging projections 632. Bone engaging projections 632 preferably have a base portion that extends from rotatable member 620 and terminates in a larger dimension upper portion. The upper portion of bone engaging projection 632 preferably has a transverse cross sectional dimension that is greater than the transverse cross sectional dimension of the base portion. By way of example only and not limitation, the base portion and the upper portion of bone engaging projection 632 can have a T-shaped cross section as shown in FIG. 19. The transverse cross sectional configuration of bone engaging projections 632 can have other configurations, including but not limited to, C-shaped, V-shaped, W-shaped, Y-shaped, and any other configuration suitable for the intended purpose. Bone engaging projections 632 preferably have a leading edge 633 that is at least in part curved and the upper portion of bone engaging projection 632 is preferably tapered proximate leading edge 633 to facilitate penetration of bone engaging projection 632 into the bone of the vertebral bodies. Similarly, openings 618 preferably have a configuration shaped to permit bone engaging projections 632 to extend from hollow interior 614 of housing 601 and through openings 618 when deployed.

Implant 600 is inserted into the disc space and bone engaging projections 632 are deployed to penetrably engage the bone of the adjacent vertebral bodies. The configuration of bone engaging projections 632 provide for increased stability of the implant relative to the adjacent vertebral bodies and of the vertebral bodies relative to each other. Further, the configuration of bone engaging projections 632 limit the ability of the vertebral bodies to move apart from one another to further enhance stability.

As shown in FIG. 20, in a further variation, the upper portion of the T-shaped configuration of bone engaging projections 632' increases in thickness at least in part from leading edge 633' to trailing edge 635' so that it is closer to the housing of implant 600 in the deployed position and brings the vertebral bodies closer together so as to compressively load the vertebral bodies towards the implant when the bone engaging projections are fully deployed. In this configuration the upper portion of bone engaging projection 632' has a decreased distance from housing of the implant at its trailing edge than at its leading edge when the bone engaging projections are in the deployed position.

As shown in FIG. 21, in a further alternative configuration, bone engaging projections 632" have a lower portion opposite the upper portion of the T-shaped configuration. The lower portion of the T-shaped configuration has an arc of radius that is less than the arc of radius of the upper portion of the T-shaped configuration resulting in a decreased distance from the housing of the implant proximate trailing edge 635" than proximate leading edge 633" when bone engaging projections 632" are in the deployed position. Such a configuration of bone engaging projections 632" provides for the compressive loading of the vertebral bodies towards the implant when the bone engaging projections are fully deployed.

In FIGS. 22 and 23, another preferred embodiment of the implant of the present invention is shown and generally referred to by the reference number 700. Implant 700 is similar to implant 600 except for the configuration of housing 701. Each of upper and lower surfaces 706, 708 of housing 701 preferably has an open area in communication with hollow interior 714 of housing 701. The open area preferably forms a window 703 (a large opening) in each of upper and lower surfaces 706, 708 over at least a portion of rotatable member 720. Rotatable member 720 is exposed to the adjacent vertebral bodies through windows 703. Rotatable member 720 may project at least in part through the windows 703 to contact the adjacent vertebral bodies. In a preferred embodiment, rotatable member 720 may protrude at least in part through windows 703 to be flush with the exterior of housing 701. Housing 701 is preferably configured to be opened to receive rotatable member 720 therein and closed to hold rotatable member 720 at least in part within housing 701. By way of example only and not limitation, housing 701 may be separable into upper and lower portions at seam 705.

Figure 24:
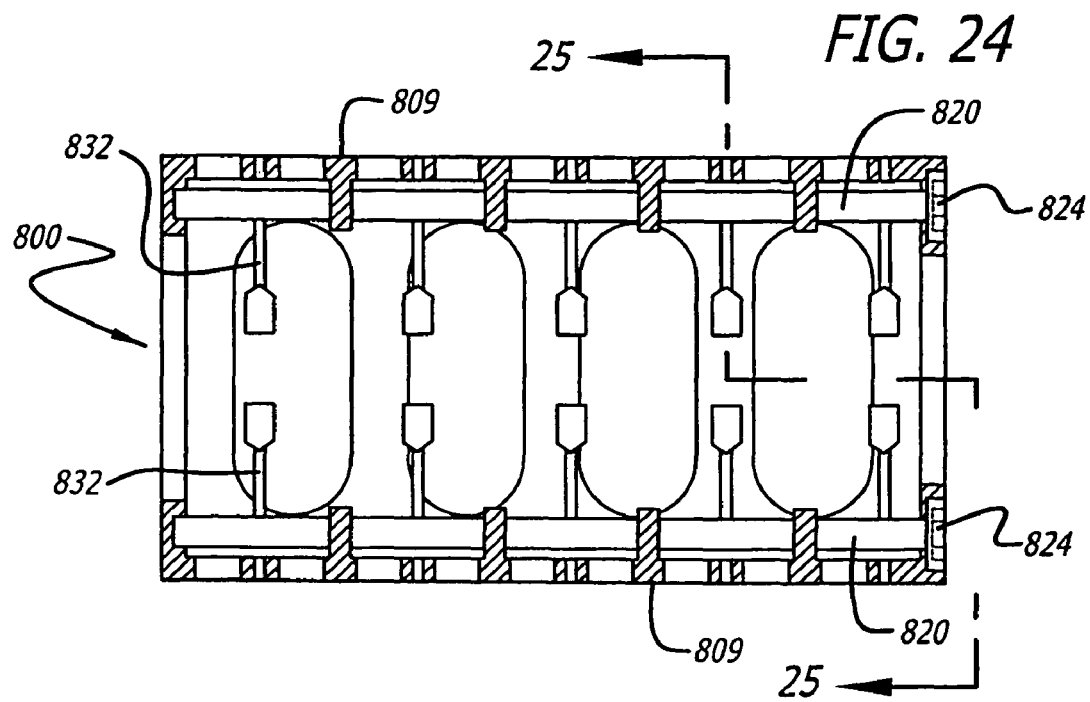
FIG. 24 is a top plan view in partial cross section of another preferred embodiment of an implant in accordance with the present invention with the bone engaging projections in a retracted position.
Figure 25:
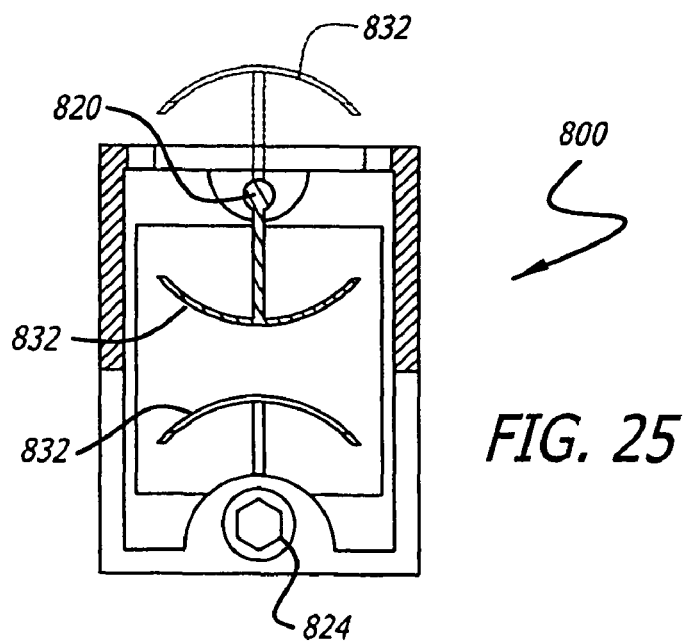
FIG. 25 a partial cross sectional end view along line 24-24 of FIG. 25 with the bone engaging projections in a retracted position shown in solid line and in a deployed position shown in hidden line.

In FIGS. 24 and 25, another preferred embodiment of the implant of the present invention is shown and generally referred to by the reference number 800. Implant 800 is similar to implant 100 except that it preferably has at least two internal rotatable members 820 for deploying bone engaging projections 832 through upper and lower surfaces 806, 808 of housing 801. Rotatable members 820 are preferably at least in part within hollow interior 814 of housing 801 proximate upper and lower surfaces 806, 808, respectively. Rotatable members 820 are preferably held in rotational relationship to housing 801 by support structures 809. Each of rotatable members 820 preferably have at least one end 824 configured to cooperatively engage an instrument for rotating rotational members 820 to deploy bone engaging projections 832. The rotation of rotatable member 820 can be in the preferred range of approximately 200 degrees to approximately 25 degrees about its axis of rotation so that it takes less than a full turn of the rotatable member to deploy the bone engaging projections. By way of example only and not limitation, rotational member 820 can be rotated more than 180 degrees, for example approximately 195 degrees, to deploy bone engaging projections 832 in an over center position. While rotational members 820 can be solid or at least in part hollow, in this instance a generally solid configuration is preferred so that each of rotational members 820 preferably has a relatively small cross sectional dimension transverse to its longitudinal axis such that rotational members 820 occupy only a small portion of the interior of housing 801.

Housing 801 of implant 800 preferably has at least a portion along its longitudinal axis that has a generally square cross section transverse to the longitudinal axis. It is appreciated that housing 801 can have a generally rectangular cross section or other cross-sectional configuration suitable for its intended purpose. The implant may be inserted into the disc space on its side and then flipped 90 degrees to orient the upper and lower surfaces of the implant toward the adjacent vertebral bodies, respectively. Such an implant would preferably have a reduced dimension between a pair of diagonally opposed corners. For example, such an implant could have diagonal corners that are rounded to facilitate the 90 degree rotation of the implant between the adjacent vertebral bodies as taught by Michelson in U.S. application Ser. No. 09/429, 628 for a "Self-Broaching, Rotatable, Push-In Interbody Spinal Fusion Implant and Method for Deployment Thereof", the portions of the specification directed to the reduced dimension between a pair diagonally opposed corners are hereby incorporated by reference herein. Upper and lower surfaces 806, 808 of implant 800 are preferably at least in part non-arcuate and are generally parallel to each other along at least a portion of the longitudinal axis of implant 800. Alternatively, upper and lower surfaces 806, 808 can be angled relative to one another along at least a portion of the longitudinal axis of implant 800.

FIGS. 1-5 show various steps of a preferred method for inserting implant 100 from a posterior approach to the spine and using associated instrumentation disclosed herein.

By way of example and not limitation, preferred steps of methods for installing the implants of the present invention include but are not limited to the steps summarized below.
1. Identifying the disc space to be operated upon;
2. Providing access to the disc space;
3. Utilizing a guard or retractor to provide protected access to the disc space;
4. Removing sufficient disc material to allow an implant to be inserted at least in part within and across the height of the disc space;
5. Distracting the disc space between the vertebral bodies to generally restore the height of the disc space with or without the use of a distractor;
6. Utilizing a guard with disc penetrating extensions to provide protected access to the disc and to distract the vertebral bodies adjacent the disc space;
7. Working upon the endplates of the adjacent vertebral bodies, which may include for example scraping the endplates, decorticating the endplates, or cutting away at least a portion of the endplates;
8. Attaching the implant to an implant inserter;
9. Inserting the implant at least in part into the disc space;
10. Loading the implant with bone growth promoting material: (i) prior to implantation of the implant, (ii) after implantation of the implant, or (iii) both prior to implantation and after implantation of the implant;
11. Packing bone growth promoting material around the implant and pushing bone through the implant and into the area around the implant;
12. Rotating the hollow internal member to deploy the bone engaging projections to penetrably engage the vertebral bodies adjacent the disc space, which may include rotating the internal member less than 180 degrees;
13. Removing the inserter from the implant; and/or
14. Repeating the procedure at same disc level if necessary.

The methods for installing the implants of the present invention are not limited to the steps identified above, need not include all the steps recited above, and need not be performed in the order listed above. By way of example only and not limitation, two implants may be inserted into the disc space before either has its internal rotatable member rotated to deploy the bone engaging projections, or the implant may be inserted into the disc space prior to being packed with bone growth promoting material or prior to the bone growth promoting material being forced through the openings in the implant. Other methods for installing implants known to those skilled in the art may be used to install the implants of the present invention may be used without departing from the scope of the present invention.

Preferred instruments and methods of preparing the disc space are disclosed and taught by Michelson in U.S. Pat. No. 6,159,214 entitled "Milling Instrumentation and Method for Preparing a Space Between Adjacent Vertebral Bodies"; U.S. Patent Application No. 60/255,463 entitled "Spinal Interspace Shaper"; U.S. Pat. No. 6,083,228 entitled "Device and Method for Preparing a Space Between Adjacent Vertebrae to Receive an Insert"; U.S. Pat. No. 6,224,607 entitled "Instrument and Method for Creating an Intervertebral Space for Receiving an Implant"; and WIPO publication WO 99/63891 entitled "Device for Preparing a Space Between Adjacent Vertebrae to Receive an Insert," the disclosures of which are all herein incorporated by reference. It is appreciated that other instruments and methods may be used to prepare the disc space to receive the implant of the present invention.

Where it is desirable, the surgeon may utilize a guard such as guard 500 shown in FIG. 1 for protecting adjacent delicate neurological structures. Guard 500 may be left in place after the preparation of the disc space such that the described operation can be performed through guard 500 and be removed at its completion. The implantation space may have any configuration suitable to receive the implant to be inserted therein.

Prior to preparing the disc space, if it is desirable, the surgeon may distract the vertebral bodies with a distractor having disc penetrating extensions such as that taught by Michelson in U.S. Pat. No. 5,484,437 entitled "Apparatus and Method of Inserting Spinal Implants" and U.S. Pat. No. 5,797,909 (the '909 patent), entitled "Apparatus for Inserting Spinal Implants," the disclosures of which is herein incorporated reference. If necessary, the surgeon may impart an angulation to the adjacent vertebral bodies with a distractor having disc penetrating extensions with angled upper and lower surfaces such as that taught in the '909 patent to Michelson.

As shown in FIGS. 2 and 5, rotatable member 120 may be inserted into hollow interior 114 of implant 100 and distal end 204 of inserter 200 is cooperatively engaged to trailing end 104 of implant 100 such that tabs 214 of implant engagement surface 212 are engaged with grooves 140 of implant 100. It is appreciated that rotatable member 120 may be inserted into hollow interior 114 of housing 101 after implant 100 is inserted into the disc space. Implant 100 is inserted into the disc space preferably by linear insertion without substantial rotation of implant 100 to the appropriate depth as desired by the surgeon. Alternatively, the implant be can be rotated at least in part during its implantation into the disc space, but is not screwed into the disc space. For example, the implant may be inserted into the disc space on its side and then rotated 90 degrees to place the upper and lower surfaces of housing 101 in contact with the adjacent vertebral bodies, respectively. Bone engaging projections 132 can then be deployed. Trailing end 104 of implant 100 preferably does not protrude beyond the posterior aspects of the adjacent vertebral bodies, and preferably no substantial portion of implant 100 protrudes from the outer perimeter of the adjacent vertebral bodies. During insertion of implant 100, bone engaging projections 132 are retained in the retracted position to facilitate linear insertion of implant 100 into the disc space.

After implant 100 is properly positioned in the implantation space, the bone engaging projections 132 can be deployed. In a preferred embodiment, inner shaft 224 of inserter 200 is rotated by the surgeon to rotate rotatable member 120 of implant 100 from a retracted position to a deployed position so that bone engaging projections 132 extend through upper and lower surfaces 106, 108 of implant 100 to penetrably engage the end plates of the adjacent vertebral bodies and prevent the expulsion of the implant from the disc space. In a preferred embodiment, rotatable member 120 is rotated one half turn or less to deploy the bone engaging projections.

Implant inserter 200 is detached from implant 100 and removed. A cap may be installed to close at least part of the implant's trailing end to prevent bone from growing into the spinal canal, or to limit adhesions of the neurological structures at the canal floor, or to otherwise protect the neurological structures. One of the purposes for a cap includes restricting the passage of fusion-promoting materials so that they remain loaded within the implant.

Preferably prior to insertion, hollow interior 114 of implant 100 and open interior 128 of rotatable member 120 may be loaded with fusion promoting materials including any of, or any combination of, bone in any of its forms, materials derived from bone, bone morphogenetic proteins, mineralizing proteins, genetic materials coding for the production of bone or any substance capable of inducing the formation of bone or useful for achieving fusion for the intended purpose. The fusion promoting materials may be loaded or preferably compressively loaded into hollow interior 114 of implant 100 and/or open interior 128 of rotatable member 120 by use of an instrument such as, for example, a tamp, press, or piston at any time during the procedure as desired by the surgeon. Additionally, scar tissue-inhibiting and/or antimicrobial materials may be applied to the implant.

When said methods and instrumentation are used to install such implants posteriorly, the technique may further include the application of scar tissue inhibiting substances posterior to the implant trailing end and at the floor of the spinal canal.

When performing the procedure from a posterior approach to the spine, it is generally preferred that the procedure be performed on both sides of the saggital midline of the disc space and that two implants 100, each having a width less than half the width of the disc space be inserted from a posterior to anterior approach either generally parallel or alternatively from a generally posterior to anterior approach in a "toed-in" configuration. Having completed the procedure on a first side, the procedure is then repeated as already described on the opposite side of the saggital midline of the same disc space leading to the implantation of two implants 100 in the same disc space.

If implants 300 are being inserted into the disc space, then the procedure may preferably include distracting the adjacent vertebral bodies to impart an angulation to the adjacent vertebral bodies with a distractor such as that taught in the '909 patent to Michelson to accommodate the insertion of each of implants 300. In another alternative method, both implants may be implanted from an anterior approach to the spine using many of the same steps already described.

When performing the method from the anterior approach, a plurality of implants 100 or 300 (for example two or three) or a single implant such as implant 400 may be used as the spinal cord is not in the path of insertion of the implant. When using a laparoscope or when it is difficult to mobilize the great vessels two or more smaller implants may be used in order to use a smaller working space.

The various features of the preferred embodiments of the present inventions described herein are combinable with one another and are not limited to a particular embodiment of the implant for which the features are described. By way of example only and not limitation, it is appreciated that for any of the embodiments of the implants of the present invention, the external housing may be formed of two or more pieces that can be separated to permit insertion of the internal rotatable member within the housing and then reassembled for installation into the disc space; and the various embodiments of the bone engaging projections described herein may be utilized with any of the embodiments of the implants of the present invention.

The spinal fusion implant of the present invention may comprise of any artificial or naturally occurring implant material suitable for implantation in a human being. The implant of the present invention can be formed of a material such as metal including, but not limited to, titanium and its alloys, surgical grade plastics, composites, ceramics, or other materials suitable for use as a spinal fusion implant. The implant of the present invention can comprise at least in part of a material that is resorbable by the human body. The implant of the present invention can be formed at least in part of a porous material or can be formed at least in part of a material that intrinsically participates in the growth of bone from one of adjacent vertebral bodies to the other of adjacent vertebral bodies.

Further, the implant of the present invention may be comprised of, treated with, coated, or filled with a fusion promoting substance. The implant may be used in combination with a fusion promoting substance including, but not limited to, bone, bone derived products, demineralized bone matrix, ossifying proteins, bone morphogenetic proteins, hydroxyapatite, and genes coding for the production of bone.

Where such implants are for posterior implantation, the trailing ends of such implants may be treated with, coated with, or used in combination with substances to inhibit scar tissue formation in the spinal canal. The implants of the present invention may be adapted to facilitate the electrostimulation of the implant or a portion thereof and/or of the fusion area into which they are inserted and the proximate bone thereabout. The implant of the present invention may be comprised at least in part of, coated with, or used in combination with materials to make it antimicrobial, such as, but not limited to, antibiotics, silver ions or any other substance suitable for the intended purpose.

There is disclosed in the above description and the drawings implants and instruments and methods for use therewith, which fully and effectively accomplish the objectives of this invention. However, it will be apparent that variations and modifications of the disclosed embodiments may be made without departing from the principles of the invention.

What is claimed is:

1. An interbody spinal fusion implant for implantation at least in part within and across the generally restored height of a disc space between two adjacent vertebral bodies of a human spine, said spinal implant comprising:

a housing having a leading end for insertion first into the disc space, a trailing end opposite said leading end, a mid-longitudinal axis between said leading end and said trailing end of said housing, an upper surface adapted to contact one of the adjacent vertebral bodies, a lower surface opposite said upper surface adapted to contact another one of the adjacent vertebral bodies, and a hollow interior configured to hold bone growth promoting material therein, said hollow interior being between said upper and lower surfaces and said leading and trailing ends, said housing having a horizontal plane parallel to the mid-longitudinal axis passing through said leading end and trailing end of said housing, the horizontal plane bisecting said housing into two equal parts, said upper and lower surfaces each having at least one opening therein in communication with said hollow interior and with each other to permit for the growth of bone from adjacent vertebral body to adjacent vertebral body through said hollow interior of said housing;

at least two internal rotatable members positioned at least in part within said hollow interior of said housing, a first of said rotatable members being proximate to said upper surface, a second of said rotatable members being proximate to said lower surface, each of said rotatable members having a longitudinal axis and a maximum cross-sectional dimension transverse to the longitudinal axis; and a plurality of bone engaging projections each having a base extending from each of said rotatable members and terminating at an end, said bone engaging projections adapted to penetrably engage the bone of the adjacent vertebral bodies by rotating about the longitudinal axes of said rotatable members, respectively, each of said bone engaging projections having a dimension as measured in a direction transverse to the longitudinal axes of each of said rotatable members, respectively, from said base to said end being greater than the maximum cross-sectional dimension of each of said rotatable members, said bone engaging projections being adapted to rotate within said hollow interior of said housing between a retracted position and a deployed position, at least a portion of one of said bone engaging projections being within said hollow interior of said housing when in the retracted position, said bone engaging projections of said rotatable members extending through said one of said upper and lower surfaces of said housing so as to penetrably engage the bone of the adjacent vertebral bodies when in the deployed position, said hollow interior being unobstructed by said bone engaging projections when in the deployed position to permit for the growth of bone from adjacent vertebral body to adjacent vertebral body through said hollow interior.

2. The implant of claim 1, wherein said bone engaging projections are fully contained within said hollow interior of said housing when in the retracted position.

3. The implant of claim 1, wherein said end of at least one of said bone engaging projections has a length and a width, said width of said end being greater than a width of said base.

4. The implant of claim 3, wherein at least a portion of said at least one bone engaging projection has at least one of a generally T-shaped, C-shaped, V-shaped, W-shaped, and Y-shaped configuration.

5. The implant of claim 3, wherein said end of said at least one bone engaging projection has a leading edge, a trailing edge, and a thickness that increases at least in part in a direction away from said leading edge along at least a portion of said length of said end.

6. The implant of claim 3, further comprising at least one bone engaging projection receiving opening in said upper and lower surfaces of said housing having a configuration generally corresponding to the configuration of said at least one bone engaging projection.

7. The implant of claim 6, wherein said bone engaging projection receiving openings also permit for the growth of bone therethrough.

8. The implant of claim 1, wherein at least one of said bone engaging projections has a sharp leading edge adapted to cut into bone.

9. The implant of claim 1, wherein said housing and said rotatable members cooperate so as to limit rotation of at least one of said rotatable members to no more than 180 degrees.

10. The implant of claim 1, wherein at least one of said rotatable members has a leading end and a trailing end, said trailing end of at least one of said rotatable members being configured to cooperatively engage an insertion instrument.

11. The implant of claim 1, wherein said trailing end of said housing is configured to cooperatively engage an insertion instrument.

12. The implant of claim 1, further comprising at least one arcuate portion in said upper and lower surfaces of said housing, respectively.

13. The implant of claim 1, wherein at least one of said upper and said lower surfaces of said housing is at least in part non-arcuate.

14. The implant of claim 1, wherein at least one of said leading and said trailing ends of said housing is open to permit for loading of bone growth promoting material into at least said hollow interior of said housing.

15. The implant of claim 1, wherein said hollow interior of said housing is configured to limit the degree of rotation of said rotatable members within said housing.

16. The implant of claim 1, wherein said hollow interior of said housing includes at least one abutment surface adapted to contact a portion of said rotatable members to limit the rotation of said rotatable members.

17. The implant of claim 1, in combination with a bone growth promoting material.

18. The implant of claim 1, wherein said bone growth promoting material is selected from one of bone, bone derived products, demineralized bone matrix, ossifying proteins, bone morphogenetic protein, hydroxyapatite, and genes coding for the production of bone.

19. The implant of claim 1, wherein said implant is at least in part resorbable.

20. The implant of claim 1, wherein said hollow interior of said housing is a chamber for holding bone growth promoting material.

21. The implant of claim 1, wherein at least one of said bone engaging projections is non-circular.

22. The implant of claim 1, wherein each of said rotatable members has a mid-longitudinal axis, said bone engaging projections being offset from the mid-longitudinal axes.

23. The implant of claim 1, wherein at least one of said bone engaging projections is more proximate to a plane perpendicular to the mid-longitudinal axis of said housing and bisecting said housing into two parts of equal length than to either one of said leading and trailing ends of said housing.

24. An interbody spinal fusion implant for implantation at least in part within and across the generally restored height of a disc space two adjacent vertebral bodies of a human spine, said spinal implant comprising:

a housing having a leading end for insertion first into the disc space, a trailing end opposite said leading end, a mid-longitudinal axis between said leading end and said trailing end of said housing, an upper surface adapted to contact one of the adjacent vertebral bodies, a lower surface opposite said upper surface adapted to contact another one of the adjacent vertebral bodies, and a hollow interior configured to hold bone growth promoting material therein, said hollow interior being between said upper and tower surfaces and said leading and trailing ends, said upper and lower surfaces each having at least one opening therein in communication with said hollow interior and with each other to permit for the growth of bone from adjacent vertebral body to adjacent vertebral body through said hollow interior of said housing;

at least one internal rotatable member proximate one of said upper and lower surfaces and configured to be at least in part within said hollow interior of said housing, said rotatable member having a longitudinal axis and a maximum cross-sectional dimension transverse to the longitudinal axis; and a plurality of bone engaging projections extending from said rotatable member, said bone engaging projections adapted to penetrably engage the bone of the adjacent vertebral bodies by rotating about the longitudinal axis of said rotatable member, said bone engaging projections being adapted to rotate within said hollow interior of said housing between a retracted position and a deployed position, a first of said bone engaging projections being proximate said leading end of said housing, a second of said bone engaging projections being proximate said trailing end of said housing, and a third of said bone engaging projections being between said first and second bone engaging projections along a line parallel to the longitudinal axis of said rotatable member and passing through said first, second, and third bone engaging projections, said bone engaging projections each being within said hollow interior of said housing when in the retracted position, each of said bone engaging projections extending through at least one of said upper and lower surfaces of said housing so as to penetrably engage the bone of the adjacent vertebral bodies when in the deployed position, said hollow interior being unobstructed by said bone engaging projections when in the deployed position to permit for the growth of bone from adjacent vertebral body to adjacent vertebral body through said hollow interior.

25. The implant of claim 24, wherein at least one of said bone engaging projections has a base portion extending from said rotatable member and terminating in an upper portion having a length and width, said upper portion having a width that is greater than the width of said base portion.

26. The implant of claim 25, wherein at least a portion of said at least one bone engaging projection has at least one of a generally T-shaped, C-shaped, V-shaped, W-shaped, and Y-shaped configuration.

27. The implant of claim 24, wherein said housing and said rotatable member cooperate so as to limit rotation of at least one of said rotatable member to no more than 180 degrees.

28. The implant of claim 24, wherein said hollow interior of said housing includes at least one abutment surface adapted to contact a portion of said rotatable member to limit the rotation of said rotatable member.

29. The implant of claim 24, wherein at least one of said bone engaging projections is more proximate to a plane perpendicular to the mid-longitudinal axis of said housing and bisecting said housing into two parts of equal length than to either one of said leading and trailing ends of said housing.

30. An interbody spinal implant comprising:
a body having an upper portion and a lower portion; and
first and second rotatable shafts, said body including a first set of retaining members adapted to at least partially surround said first rotatable shaft and a second set of retaining members adapted to at least partially surround said second rotatable shaft, each of said rotatable shafts including a plurality of spaced-apart bone engaging projections extending therefrom, said bone engaging projections being interspersed with said retaining members when said rotatable shafts are engaged with said retaining member, said body including a plurality of recesses interspersed with said retaining members, said recesses spacing apart said retaining members from one another, said recesses being adapted to receive said bone engaging projections, said first and second rotatable shafts each being rotatable to move said bone engaging projections through said recesses to deploy said bone engaging projections into bone, said first and second rotatable shafts being parallel to one another.

31. The implant of claim 30, wherein said first rotatable shaft is positioned at said upper portion of said implant and said second rotatable shaft is positioned at said lower portion of said implant.

32. The implant of claim 31, wherein said implant includes a leading end for insertion first into a disc space between two adjacent vertebral bodies of a human spine, a trailing end opposite said leading end, a length from said leading end to said trailing end, and a width transverse to the length, said second rotatable shaft being positioned along the length of said implant at a location that is approximately one-half the width of said implant.

33. The implant of claim 31, wherein said first and second rotatable shafts each have an axis of rotation, the axes being in a single vertical plane.

34. The implant of claim 30, wherein said implant includes a leading end for insertion first into a disc space between two adjacent vertebral bodies of a human spine, a trailing end opposite said leading end, a length from said leading end to said trailing end, each of said recesses having a minimum width along the length of said implant that is less than the thickness of each of said retaining members along the length of said implant.

35. The implant of claim 30, wherein said implant includes a leading end for insertion first into a disc space between two adjacent vertebral bodies of a human spine, a trailing end opposite said leading end, a length from said leading end to said trailing end, each of said recesses having a minimum width along the length of said implant, a pair of adjacent bone engaging projections having a distance therebetween that is greater than the minimum width of one of said recesses.

36. The implant of claim 30, wherein each of said rotatable shafts has a length, said plurality of bone engaging projections being spaced along a majority of the length of each rotatable shaft.

37. The implant of claim 30, wherein said bone engaging projections extend from only one side of each of said rotatable shafts.

38. The implant of claim 30, wherein said implant includes only four retaining members for each rotatable shaft.

39. The implant of claim 30, wherein said implant includes a leading end for insertion first into a disc space between two adjacent vertebral bodies of a human spine, a trailing end opposite said leading end, and a length from said leading end to said trailing end, said first and second sets of retaining members being located along a majority of the length of said implant.

40. The implant of claim 30, wherein each of said bone engaging projections has a base terminating in a head, each of said first and second rotatable shafts being rotatable to move said head completely out of said recess.

41. The implant of claim 30, in combination with hydroxyapatite.

42. The implant of claim 30, wherein said implant is a spinal fusion implant.

43. The implant of claim 30, wherein said implant includes a hollow interior, said plurality of recesses being in communication with said hollow interior.

44. The implant of claim 30, wherein said implant includes a hollow interior, at least said first set of retaining members being located at least in part within said hollow interior.

45. An interbody spinal implant comprising:
a body having an upper portion and a lower portion; and
first and second rotatable shafts, each of said first and second rotatable shafts having an axis of rotation, said body including a first set of retaining members adapted to at least partially surround said first rotatable shaft and a second set of retaining members adapted to at least partially surround said second rotatable shaft, each of said rotatable shafts including a plurality of spaced-apart bone engaging projections extending from only one side of said shaft, said bone engaging projections being interspersed with said retaining members when said rotatable shafts are engaged with said body, each of said bone engaging projections including a base terminating in a head, said head having an arcuate outer perimeter terminating at a first end and a second end, the entirety of said arcuate outer perimeter extending less than one-half of a circle in a plane transverse to the axis of rotation of said rotatable shaft, said first and second rotatable shafts each being rotatable to deploy said bone engaging projections into bone.

46. The implant of claim 45, wherein said first and second rotatable shafts are each rotatable to move said bone engaging projections from an undeployed position where a majority of said arcuate outer perimeter is within a portion of said implant to a deployed position where the entire arcuate outer perimeter is exposed.

47. The implant of claim 45, wherein said first end is a leading end and said second end is a trailing end so that said first end penetrates bone before said second end when said bone engaging projection is deployed, each of said rotatable shafts being rotatable to expose said second end.

48. The implant of claim 45, wherein each rotatable shaft has a diameter, said arcuate outer perimeter of said head having an apex, each of said bone engaging projections having a length measured from the axis of rotation of said rotatable shaft to said apex, the length of at least one of said bone engaging projections being greater than the diameter of said rotatable shaft adjacent said at least one bone engaging projection.

49. The implant of claim 45, wherein each rotatable shaft has a diameter, said first and second ends of said arcuate outer perimeter of said head having a distance therebetween greater than the diameter of said rotatable shaft adjacent one of said bone engaging projections.

50. The implant of claim 45, wherein each rotatable shaft has a diameter, said arcuate outer perimeter of said head having an apex, each of said bone engaging projections having a length measured from the axis of rotation of said rotatable shaft to said apex, said first and second ends of said arcuate outer perimeter of said head lying in a plane, the plane intersecting the length of said bone engaging projection.

51. The implant of claim 50, wherein said arcuate outer perimeter has a distance therealong that is greater than the length of said bone engaging projection.

52. The implant of claim 45, wherein each rotatable shaft has a diameter, said arcuate outer perimeter of said head having an apex, each of said bone engaging projections having a length measured from the axis of rotation of said rotatable shaft to said apex, said base having a width transverse to the length of said bone engaging projection, said first and second ends of said arcuate outer perimeter of said head having a distance therebetween greater than the width of said base.

53. The implant of claim 45, wherein said head includes a blade portion, said blade portion being oriented toward said body of said implant once said bone engaging projection has been moved into a deployed position.

54. The implant of claim 45, wherein each of said rotatable shafts includes a root diameter and an enlarged head with an instrument engagement area, said enlarged head having a diameter substantially larger than the root diameter of said rotatable shaft.

55. The implant of claim 45, wherein said first rotatable shaft is positioned at said upper portion of said implant and said second rotatable shaft is positioned at said lower portion of said implant.

56. The implant of claim 55, wherein said implant includes a leading end for insertion first into a disc space between two adjacent vertebral bodies of a human spine, a trailing end opposite said leading end, a length from said leading end to said trailing end, and a width transverse to the length, said second rotatable shaft being positioned along the length of said implant at a location that is approximately one-half the width of said implant.

57. The implant of claim 45, wherein the axes of rotation of said first and second rotatable shafts are in a single vertical plane.

58. The implant of claim 45, wherein each of said rotatable shafts has a length, said plurality of bone engaging projections being spaced along a majority of the length of each rotatable shaft.

59. The implant of claim 45, wherein all of said bone engaging projections have the same shape.

60. The implant of claim 45, wherein said bone engaging projections of one of said first and second rotatable shafts are each parallel to one another.

61. The implant of claim 45, in combination with hydroxyapatite.

62. The implant of claim 45, wherein said implant is a spinal fusion implant.

63. The implant of claim 45, wherein said implant includes a hollow interior, at least said first set of retaining members being located at least in part within said hollow interior.

* * * * *

UNITED STATES PATENT AND TRADEMARK OFFICE
CERTIFICATE OF CORRECTION

| | | |
|---|---|---|
| PATENT NO. | : 7,771,475 B2 | Page 1 of 1 |
| APPLICATION NO. | : 11/527377 | |
| DATED | : August 10, 2010 | |
| INVENTOR(S) | : Gary K. Michelson | |

It is certified that error appears in the above-identified patent and that said Letters Patent is hereby corrected as shown below:

Column 18:
Line 52: after "space" insert -- between --; and
Line 63: change "tower" to -- lower --.

Signed and Sealed this
Thirteenth Day of September, 2011

David J. Kappos
*Director of the United States Patent and Trademark Office*